US006391624B1

(12) United States Patent
Megerle (10) Patent No.: US 6,391,624 B1
(45) Date of Patent: May 21, 2002

(54) HIGHLY SENSITIVE BIOLOGICAL AGENT PROBE

(75) Inventor: Clifford A. Megerle, Thousand Oak, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 09/585,549

(22) Filed: Jun. 2, 2000

Related U.S. Application Data

(60) Provisional application No. 60/137,597, filed on Jun. 3, 1999, and provisional application No. 60/154,037, filed on Sep. 16, 1999.

(51) Int. Cl.[7] .......................... C12M 1/34; C12M 1/42; C12Q 1/68; C12P 19/34; G01N 15/06

(52) U.S. Cl. ................... 435/287.2; 435/285.2; 435/287.1; 435/6; 435/91.1; 422/68.1

(58) Field of Search .................... 435/6, 91.1, 91.2, 435/183, 283.1, 287.1, 287.2, 285.2; 436/94; 536/23.1, 24.3, 24.33, 25.3; 422/50, 82.01, 82.02, 82.05, 82.08, 82.11, 68.1

(56) References Cited

U.S. PATENT DOCUMENTS 5,670,322 A    9/1997  Eggers
5,741,644 A *  4/1998  Kambara et al. ............... 435/6
5,871,918 A *  2/1999  Thorp et al. .................... 435/6
5,874,046 A *  2/1999  Megerle ..................... 422/68.1
6,030,781 A *  2/2000  Shieh ............................. 435/6

* cited by examiner

*Primary Examiner*—Ethan C. Whisenant
*Assistant Examiner*—Frank Lu
(74) *Attorney, Agent, or Firm*—Venable; Andrew C. Aitken (57) ABSTRACT

An improved biological probe is disclosed that employs a plurality of groups of modified single-stranded DNA attached to a single electrode. Using a plurality of such groups increases the inherent sensitivity of the probe by providing additional hybridization location sites and also serves to improve performance by diminishing steric hindrance caused by the crowding and tangling of the long single-stranded oligionucleotide molecules. The modification of the oligionucleotides involves the attachment of electron donor and acceptor moieties that alters the electrochemical properties of the hybridized molecules. The selected groups of modified oligionucleotides are complementary to unique characteristic sequences of the target DNA or RNA. A sample that containing oligionucleotides of a target biological agent is brought into contact with the probe and complementary portions of the molecules will hybridize with the oligionucleotides attached to the probe. When voltage is applied to the electrode, current will flow through the hybridized molecules with little resistance. Measurement of the current or changes in the current within the probe will indicate the presence of target DNA or RNA.

18 Claims, 6 Drawing Sheets

HIGHLY SENSITIVE BIOLOGICAL AGENT PROBE

CROSS REFERENCE TO RELATED APPLICATION

This application claims the priority of U.S. Provisional Application Nos. 60/137,597, filed Jun. 3, 1999 and 60/154,037, filed Sep. 16, 1999.

TECHNICAL FIELD OF THE INVENTION

This invention relates to an improved probe which detects the presence of biological material and, more particularly, a probe designed to detect the presence of preselected DNA or RNA segments which are characteristic of a particular biological agent at very low levels.

BACKGROUND OF THE INVENTION

The ability to remotely and automatically detect the presence of specific molecular structures, and particularly the presence of a biologically active structures, is desirable in connection with a wide variety of applications. In environmental and battlefield applications, it is desirable to provide probes which can rapidly detect the presence of highly virulent bacteria, viruses or other organisms which pose a threat to human health. Remote detection of the presence of characteristic deoxyribonucleic acid (DNA) of an organism or virus would enable a highly accurate identification of a biological agent without entering the immediate environment harboring the substance. In view of the potential for the agent to be widely dispersed in air or water, it is also desirable to be able to detect the presence of potential pathogens at very low levels. The detection of pathogens at very low levels can provide an early warning so that responsive protective measures may be quickly implemented. For example, the remote detection of an environmentally released cloud of a biological agent is of vital importance to the military.

A further application where the rapid and accurate detection of low levels of DNA is desirable is in connection with the diagnosis of disease. Biologically active agents, including bacteria and viruses which may cause disease, can be identified by their unique DNA sequences. The rapid and accurate identification of a pathological biological agent from a culture, biopsy or blood sample can assist in the diagnosis of disease and accordingly facilitate an appropriate treatment of a patient by health care professionals at the earliest opportunity. The rapid and accurate detection of the presence of particular segments of DNA or RNA (ribonucleic acid) segments also has applications in connection with genetic screening and in connection with new drug development. For example, probes may be employed for a rapid determination of viral titer in samples after being treated with antiviral or anti-bacterial drugs under investigation to assess their efficacy.

Conventional techniques for identification of unknown biological agents which are frequently invoked include assays which employ antigen-antibody reactions. Although the antibody-antigen assays provide a rapid response, they are not particularly accurate, because often antibodies are not highly specific will bind with more than one antigen. Furthermore, all such assays are not particularly sensitive when only very low levels of the antigen are present. Sensitivity is an assay's ability to make a detection at very low levels of sample material. In some circumstances it is feasible to culture samples containing unknown organisms to increase the volume available for subsequent inspection and testing by trained laboratory technicians, however these procedures are time consuming, expensive and often not practical. Other traditional assay techniques involve the basic physical measurements of the molecular structures of an unknown sample by optical techniques, mass spectroscopy or nuclear magnetic resonance. These physics-based detection techniques attempt to identify the unknown material by pattern matching against the large databases of known material parameters that have been accumulated over the years. Although these techniques can provide a rapid response, these chemical and biological sensors are often large (e.g., table-top to room-sized), are not highly sensitive or accurate, and require expensive laboratory equipment.

One problem with employing these conventional detection technologies is that they require relatively large volumes of the unknown agent, and due to collection techniques, or because the concentration in the sample of a target organism or virus is very low, the identification methods are not sensitive enough to provide for an accurate positive identification. For example, the concentration of the target biological agent in a sample may be very small in view of a wide dispersal and consequent dilution of the agent in air or water. A further problem and concern with conventional detection technologies is the time necessary to make a positive and accurate identification. The ability to make a real time identification of highly virulent agents would enable the implementation of an immediate and appropriate response.

The advent of polymerase chain reaction or PCR technology has significantly advanced many of the problems associated with the problems with very small sample sizes. The PCR process provides a relative rapid and accurate manner to amplify any DNA within a sample and the process has been incorporated into automated systems for the amplification and detection of nucleic acid sequences for infectious agents. Development efforts are presently underway which combine the PCR process and miniaturization of mechanical components such as putting an electrophoretic, optical or mass spectrometer detector-on-a-chip along with fabricating the adjunct microfluidic components, such as tiny valves and pumps, which are necessary to configured an integrated DNA amplifier and detector. Other related amplification techniques include ligase chain reaction, strand displacement amplification, transcription-associated amplification and nucleic sequence-based amplifications.

Although PCR technology addresses some of the problems with insufficient or inadequate sample size and thereby can improve sensitivity, the integration of these process typically increases the time necessary to complete the identification process. Use of the PCR process essentially forecloses the ability to make detections in real time because it requires successive amplification steps. Further, although PCR provides a solution for problems associated with low sample volumes, the technology does not directly address the identification or detection step. Utilization of PCR technology can reduce the time and increase the accuracy compared with conventional assay techniques however the protocols remain complex, there are contamination problems and the process is time consuming and costly.

A number of gene detection techniques involve the hybridization of target DNA with a complementary nucleic acids sequence on a probe. In such ligase-assisted gene detection reactions, specific DNA or RNA sequences are investigated by using them as guides for the covalent joining of pairs of complementary probe molecules. Identification techniques which employ such hybridization steps generally have a high degree of accuracy and can provide a rapid identification of the biological agent. Although these hybridization techniques are highly specific, the low sensitivities of the probes remain a problem associated with these methods. For example, one approach using hybridization of complimentary nucleic acid sequences deals with the sensitivity problem employs PCR-based methodology to amplify the target nucleic acid sequence. The PCR process is followed by a biotinylation step. The amplified products are then captured on a substrate consisting of oligonucleotide-coated paramagnetic microparticles. The detection step employs an avidin-horseradish peroxidase conjugate. Hybridized molecules can be detected by binding to an avidin enzyme complex resulting in a colored product which indicates the presence and/or position of the biotinylated probe.

A further detection technique which employs the hybridization of nucleic acids involves the attachment of fluorescent or radioactive markers on DNA molecules. Hybridization proceeds with oligonucleotides attached to a chip where the locations of particular oligonucleotides have been previously identified. Any DNA in die hybridization mixture flows over the probe and forms a bond to any sites that mimic the opposite strand from which they have a complementary sequence. In one example, when die bonding step is completed, a technician moves the chip into an automated reader where a laser scans the slide row by row, exciting the fluorescent molecules. A computer can then record the pattern of bright and dim blocks, indicating which probes found matching DNA in the test sample. By comparing the pattern to a map of known probe locations, this system can identify unknown genetic sequences.

A disadvantage to the use of markers in the detection step is that the radioactive materials and flourescent dyes have mutagentic properties. The synthesis of the probes requires a step attaching the markers to the oligonucleotides which exposes the technician to potentially hazardous substances. Besides the handling dangers in the synthesis of the probes, the ultimate disposal of the assay also remains a concern. These techniques also suffer from sensitivity problems particularly when the target DNA in the sample is very low.

A further biological agent sensing technology which employs hydbridization of DNA or RNA molecules involves the use of an array of microcantilever beams on a chip to which biological materials are selectively attracted. The attachment of the agent to a specific microcantilever can then be detected through measurable changes in its mechanical behavior, specifically, its vibration resonance frequency. Larger matrix arrays of cantilevers can be fabricated and individual beams selectively coated with oligonucleotides by applying electrical voltages only to the selected beam or beams while flooding the chip with the oligonucleotides. Washing and flooding with another oligonucleotide, and a different pattern of applied voltages, can be repeated until the whole array is loaded. When the chip is exposed to an unknown (but anticipated) nuclear material, hybridization will take place only at the locations prepared specifically for that material, which can then be determined by surveying the mechanical properties of the individual locations in the array. Other approaches using hybridization include surface plasma resonance (See Peterlinz, K. A., Georgiadis, R. M. Herne, T. M. and Tarvol, M. J. (1997) Observation of hybridization and Dehybridization of Thiol-Thethered DNA Using Two-Color Surface Plasma Resonance Spectroscopy. *J. Am. Chem. Soc.* 119, 3401–3402) or quartz crystal microbalance (See Okahata, Y. Matsunobo, Y., Ijiro, K. Mukae, M. Murakmi, A., and Makino, K. (1992), Hybridizatioin of Nucleic Acids Immobilized on a Quartz crystal Microbalance, *J. Am Chem Soc.* 114, 8299–8300). These publications are hereby incorporated by reference.

As disclosed by Meade et al. in U.S. Pat. No. 5,591,578 entitled Nucleic acid Mediated Electron Transfer, oligonucleotides may be modified with electron donor and acceptor moieties prior to attachment to an electrode. As previously discussed, an oligonucleotide having a nucleotide sequence complementary to a target nucleotide sequence in the DNA of an organism will hybridize with its complementary region located within the DNA strand. The technique disclosed by Meade, which results in a covalent attachment of the moiety to the ribose backbone of a DNA or RNA molecule, only minimally interferes with the molecular structure and the modified molecules retain their characteristic base pairing ability. Megerle disclosed a biological agent probe in U.S. Pat. No. 5,874,046 which can be constructed using this technology which involves the attachment of a plurality of these modified oligonucleotides to an electrode. The Megerle patent is hereby incorporated by reference. In the event target DNA is brought into contact with the probe, multiple hybrids can form on a single electrode, one for each oligonucleotide bound to the electrode under ideal conditions. The probe disclosed by Megerle takes advantage of the changes in the electrical properties of the modified hybridized molecules which results from the base pair bonding. When voltage is applied to the electrode, current will flow through the modified hybridized molecules with little resistance. Measurement of the current, or changes in the current within the sample cell can indicate the presence of target DNA.

Although this technique is both highly accurate and rapid, it nevertheless requires a sufficient sample available in the hybridization mixture to make detection measurements and, when the number of hybridized pairs of the modified molecules is very low, the presence of the target DNA is difficult to detect. When the number of hybridized pairs is very low, electrical current flowing between the electrode and through the electron donor or acceptor group may be to low for the electrical circuitry of the detection device to detect. In addition to the sensitivity problems which are inherent when only small samples are available to test, the sensitivity of probes using hybridization techniques are further adversely affected by steric hindrance of the target nucleotide molecules. In this regard, when the relatively long molecules of denatured single stranded DNA bind with the oligonucleotides attached to the electrode, segments of the molecule on the free ends which did not bind may physically interfere with the ability of additional molecules to hybridize with neighboring oligonucleotides.

Accordingly, it is an object of the invention to provide a highly accurate and highly sensitive probe which can make a rapid detection of the presence of target DNA or RNA. A further object of the invention is to provide to an accurate and sensitive probe which can rapidly detect the presence of potential pathogens A further object of the invention is to provide a biosensor device which can automatically and remotely sample the environment and communicate an output relating the presence or absence of a particular target DNA or RNA. Yet a further object of the invention is to provide an improved sensor cell for a biological agent probe with heightened sensitivity.

SUMMARY OF THE INVENTION

The present invention addresses some of the problems of the prior art and more particularly, is directed at improving the sensitivity of the biological probes such as those disclosed in the patent to Megerle U.S. Pat. No. 5,874,046 (hereinafter the Megerle Patent). As disclosed in the Megerle Patent, real time, or close to real time detection of microorganisms can be achieved by employing modified, single-stranded oligonucleotide sequences within a probe which are complementary to characteristic segments in target DNA or RNA. The modification of oligonucleotides by the attachment of electron donor and acceptor moieties can significantly alter the electrochemical properties of the molecule upon hybridization. As disclosed by Meade et al., upon hybridization of the probe DNA which have been modified and target DNA, the conductivity of the hybridized molecule dramatically increases and the conductivity may be detected by electrochemical measuring techniques. While Megerle previously taught the attachment of a plurality of identical oligonucleotides sequences to a single electrode employing the modification technique disclosed by Meade et al., the present invention involves attachment of a plurality of different oligonucleotide groups, each group having a multiple members with identical nucleotide sequences, to a single electrode. Providing a plurality of unique complementary oligonucleotide groups to a single electrode increases the sensitivity of the probe by both diminishing the steric hindrance effects on the surface of the probe such as crowding and tangling and by providing more potential bonding sites per molecule of the target DNA. These characteristics result in a probe having increased sensitivity and which is particularly effective for the detection of DNA or RNA of target biological agents at very low levels. A method of construction of probes having multiple groups of oligonucleotide on a single electrode groups and the operation of such probes in connection with the detection of different target biological agents is also disclosed. The invention provides both a highly accurate identification technique which is sensitive at very low levels and, by employing a hybrid pair which is capable of mediated electron transfer, provides rapid results.

DETAILED DESCRIPTION OF A PREFERRED EMBODIMENT

Figure 1:
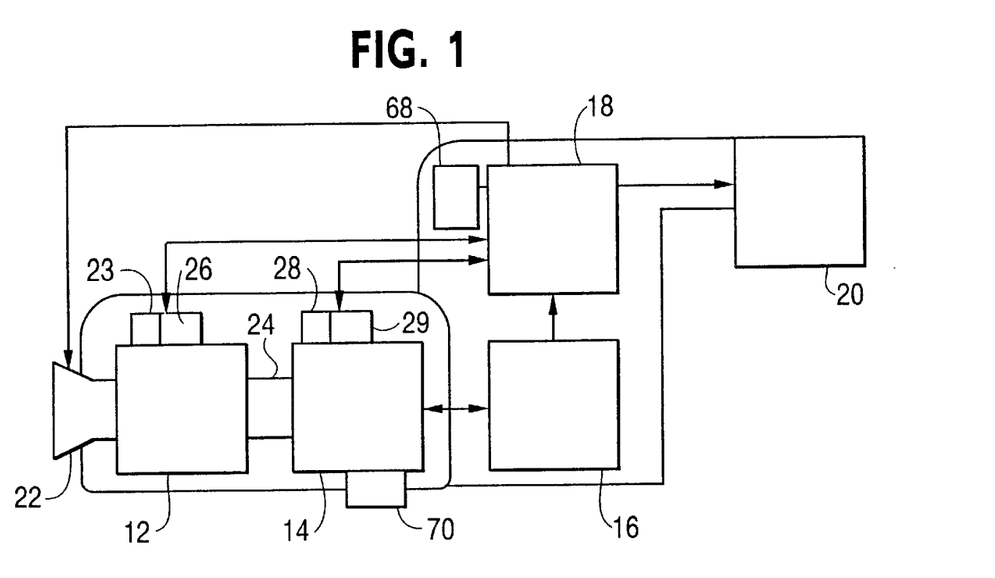
FIG. 1 is a schematic representation of a biosensor assembly system according to the invention.

Referring now to FIG. 1, a schematic representation of a biological sensor assembly according to the present invention depicts a preparation chamber 12, a sensor cell 14, a detection device 16, a central processing unit 18 and an output 20. Intake port 22 is designed to capture a sample from the external environment and convey the sample to preparation chamber 12. If the target of the sensor is an airborne biological agent such as an endospore, the intake port may incorporate a wetted wall or other cyclone, a virtual impact or and collection fluids, or a vacuum, a filter and a manner in which to backwash the filter at intermediate intervals to provide a sample to the preparation chamber. When the environment sampled is water, the inlet port may be provided with a valve and pump controlled by a microprocessor 18 to intermittently uptake fluid thereby creating a sample. In the event the sample is harvested from air, or if additional liquid is required to allow for the sample to adequately flow within the assembly, ultrapure water, reagents or buffering agents are introduced to the sample in connection with the inlet port 22.

In sample preparation chamber 12 an unknown sample is initially processed to release any DNA which may be in the sample into solution. In circumstances where the target is a prokaryotic cell such a bacterium, cell lysis is initiated. Cell lysis, which involves rupturing the phospholipid bilayer of the cell membrane, can be achieved by a variety of methods including by osmotic pressure, the introduction of enzymes or chemical agents such as aldehydes, the application of ultrasonic energy, heat or other physical energy. Upon completion of the lysis step, any DNA present in the sample, as well as other intracellular matter is released into solution. The lysate material may then be purified to selectively extract DNA at this juncture such as by implementing a plasmid purification step. Thus, in a contemplated embodiment the sample preparation chamber may further comprises a centrifuge, the reagents used to separate chromosomal DNA from plasmid DNA and any necessary additional hardware required to automatically manipulate the sample.

In circumstances where the targeted biological agent is dispersed by endospores such as anthrax (and other clostridium and bacillus bacteria), the dormancy of the spore must be interrupted prior to the lysis process causing the spore to lose its physiological properties which enable it to withstand environmental stress. After the dormancy is broken, usually by heat and moisture, germination is initiated which may further require the presence of specific stimulants in the preparation chamber such as amino acids, sugars and nucleotides. In a further alternative embodiment where the target biological agent is a virus, processes are implemented at this initial juncture to remove the protein coat encapsulating the virus.

Microprocessor 18 controls the introduction of materials from reservoir 23 which are required for the release of the DNA in the sample preparation chamber and controls and receives input from monitor 26 regarding the process conditions such as temperature and pH. Because the process conditions required to free DNA from a sample for a particular target biological agent may be unique, these parameters are previously determined for the target DNA and then programed within the microprocessor 18. In other words, depending on the nature of the organism or virus which is targeted by the probe, the sample preparation chamber is provided with the elements required to automatically extract DNA and any process conditions are controlled by the microprocessor 18.

Upon completion of the lysis step, any DNA which has been released into solution is next denatured wherein double helical DNA molecules are reduced to single-stranded DNA molecules by breaking the hydrogen bond between complementary Watson-Crick base pairs. The denaturing step, which also takes place in preparation chamber 12, results in the loss of the secondary and tertiary structure of the DNA molecule and as a result, long, single stranded molecules are created. The denaturing step can be accomplished by application of elevated temperature, pH, detergents, organic solvents and other well known manners. Although breaking the hydrogen bonds results in the dissociation of the helical structure, the phosphodiester bonds between adjacent nucleotide base pairs are maintained, and as a result, long single-stranded DNA molecules are released into the solution. Upon completion of the denaturing step, the sample is referred to as the hybridization mixture or hybridization solution.

Figure 2:
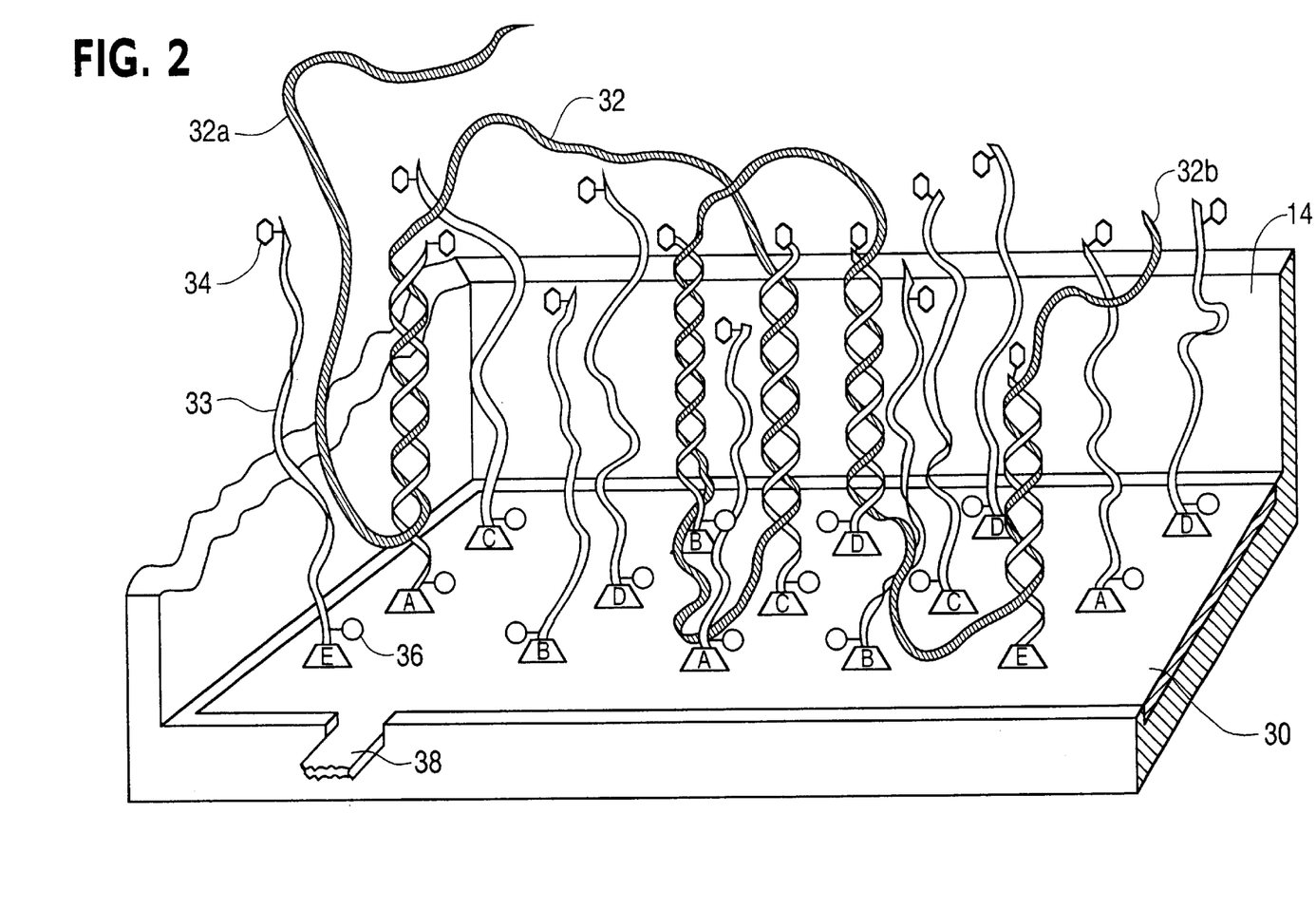
FIG. 2 is a schematic representation of a biosensor using the sensor cell according to the invention.

The hybridization mixture is physically introduced to sensor cell 14 by conduit 24 which connects the sample preparation chamber 12 to sensor cell 14. Like preparation chamber 12, process conditions within sensor cell 14, such as temperature, are monitored by sensors 28 and controlled by element 29 by microprocessor 18 to conform with the optimal hybridization conditions for the target segments. As seen in FIG. 2, an illustration of a sensor cell 14 according to the invention is depicted having a total of five distinct groups of modified oligonucleotide molecules and identified as A through E. In FIG. 2 a total of fifteen probe oligonucleotides is depicted on the surface of the electrode however in an actual sensor cell the number of oligonucleotides bound to the electrode may number from thousands to tens of thousands. Each oligonucleotide when attached to the electrode 30 is a single-stranded molecule, such as represented by reference numeral 33 and may consist of DNA or RNA. Members of the five groups are evenly and randomly distributed across the surface of electrode 30. Although in the illustration five distinct oligonucleotides are represented, any number of distinct groups greater than two will provide the advantages of the invention with respect to the enhanced sensitivity feature. As a practical matter, it is contemplated that the number of distinct groups of oligonucleotides in the preferred embodiment may number from three to ten. Electrode 30 is preferably formed of gold, indium tin oxide (ITO) or other highly conductive material and has a lead 38 which connects the electrode to the detection instrument. The other electrodes, not shown, are positioned to allow for contact with fluid contained within the sensor cell.

As illustrated in FIG. 2 the portions of a target DNA molecule 32 adjacent to a complementary oligonucleotides of the probe have hybridized. A single target molecule 32 is shown hybridized with five separate oligonucleotides which extend from the surface of the electrode. The opposite ends of the target molecule 32 extend from oligonucleotide A and oligonucleotide E. As illustrated in this example, providing five has increased the sensitivity of the sensor cell by a factor of five. If there were a total of 100 identical DNA target molecules from 100 target organisms available within the hybridization mixture, the total theoretical number of hybridized pairs would equal 500. Also illustrated in FIG. 2 is an electron donor moiety 34 attached to an oligonucleotide 33 near the free terminal end and an acceptor moiety 36 near the opposite end which is attached to the surface of electrode 30.

Figure 3:
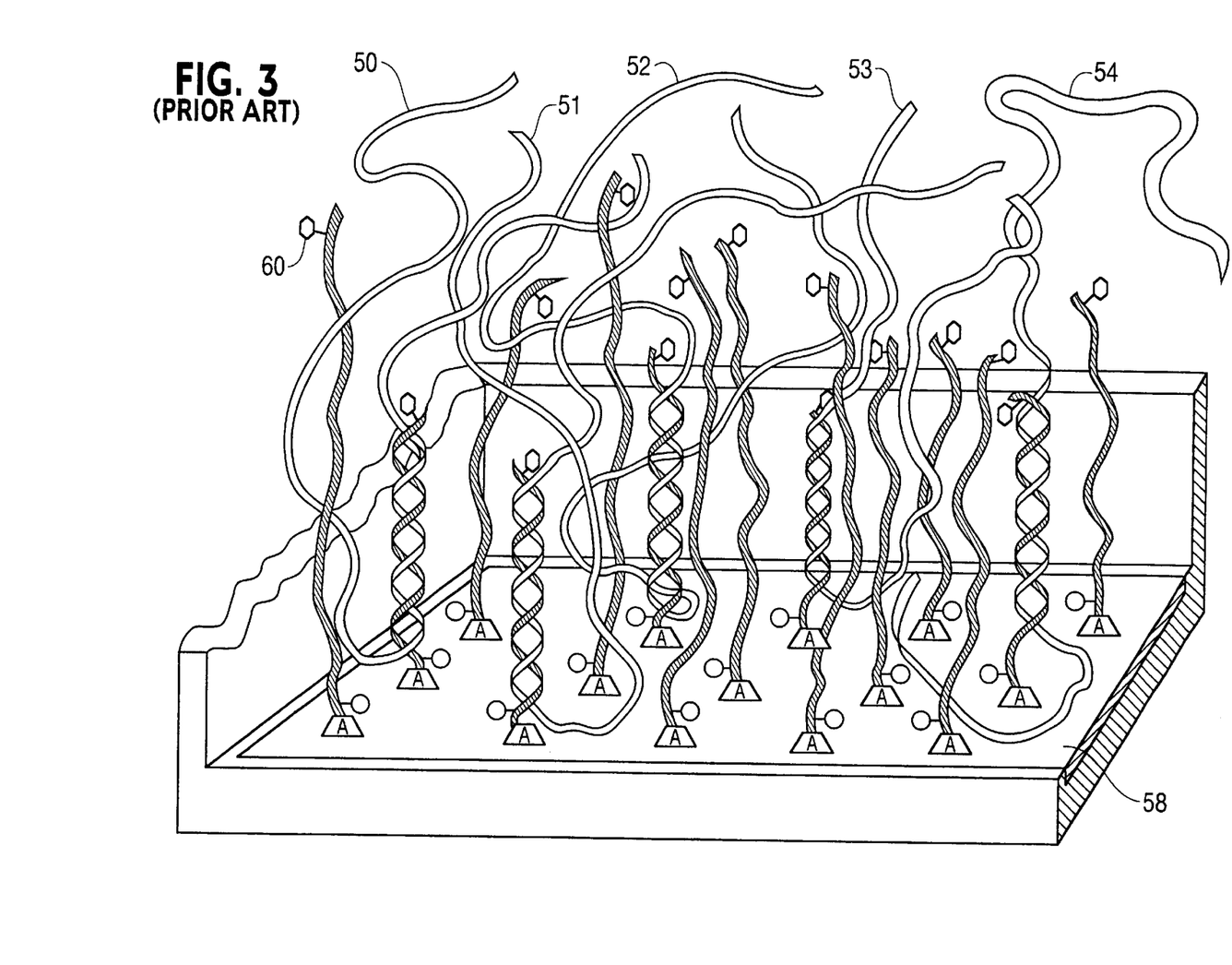
FIG. 3 is a schematic representation of a sensor cell according to the teachings in the prior art and depicting target DNA bonded to the oligonucleotide groups and exhibiting steric hindrance.

FIG. 3 illustration a probe as taught by the prior art having a multiple identical oligonucleotide groups attached to an electrode 58. Target DNA sequences from five separate DNA molecules, identified by reference numerals 50 through 54, have hybridized with five probe oligonucleotides. Each oligonucleotide attached to the electrode 58 is identical, and like the oligonucleotides according to the invention, have an electron donor 60 or acceptor group 61 attached at or near the terminal ends. In contrast with the illustration set forth in FIG. 2, although the total number of sites which have successfully hybridized is equal, there is a considerable amount of DNA which has not bonded and remains in close proximity to the probe's surface. The existence of these adjacent non-bonded sections can physically interfere with the ability of additional DNA segments present in the in hybridization mixture from hybridizing with neighboring oligonucleotides bound to the electrode. Moreover, the free ends on opposite sides of the hybridized section may seek to bond with other DNA molecules present in the hybridization mixture or bind with one another. In either scenario the sections which are not bonded and therefore do not contribute to the efficacy of the probe nevertheless increase crowding and tangling at the probe surface. As a result of these effects, the sensor cell of the probe as illustrated in FIG. 3 is less sensitive when compared to the sensor cell according to the invention.

As shown in FIG. 3, in order to achieve five hybridized base pairs, five separate DNA molecules are required in the hybridization mixture which contain the target sequence. Consequently, when the target DNA is intended to identify a bacteria, requires five organisms are required. In contrast, the probe constructed according to the invention and illustrated in FIG. 2. theoretically creates a total of five hybridized base pairs with DNA from a single target organism as shown in FIG. 2. The probe as depicted in FIG. 2 has an increased sensitivity by a factor of five when compared to the sensor cell depicted in FIG. 3.

In the hybridization step, the modified oligonucleotides attached to the electrode join with a complementary strands in the hybridization mixture through base pairing. The hybridization step typically requires temperatures between 30°–70° C. An agitator may be provided within the sensor cell in order to agitate the solution to maintain the homogeneity of the hybridization suspension and facilitate base pairing. Otherwise, diffusion may be relied upon.

In order to construct the sensor cell 14 component of the biosensor assembly, a plurality of characteristic nucleic acid sequences from a target organism are identified and oligonucleotide groups complementary to those sequences are synthesized. The synthesized groups may then be amplified using the PCR process in separate synthesis procedures. From information from the genome of the organism or virus which is to be the target of the probe, sequences are selected, typically between 15 and 100 base pairs in length. Prokaryotic organisms have a circular DNA and plasmids which typically contain characteristic DNA suitable for selection as a target sequences. Virulence genes of pathogenic bacteria, which are typically characteristic of the pathogen and code for toxins, adhesins, invasins or other virulence factors, may be located on transmissible genetic elements such as transposons, plasmids or bacteriophages. In addition, such virulence genes may be part of particular regions on the bacterial chromosomes, termed "pathogenicity islands." These pathogenicity islands comprise relatively large DNA regions (up to 200 kb of DNA) and often carry more than one virulence gene. All may be appropriate for selection as the target sequences. Pathogenicity can also be carried on plasmids, short circular DNA molecules independent of a bacterium's genomic DNA. Optimally, the target sequences selected should be on the same side or same chain of a single stranded DNA molecule. This selection is preferred because it allows for more hybridization from a single DNA molecule of a target organism. Although theoretically, the nucleic acid sequences found on opposite sides of the double helical molecule on a target organism would be present in the hybridization solution after the denaturation procedure, it is believed that the hybridization of a portion of a single molecule will increase the chances that a neighboring section on the molecule will also find its complementary sequence on the probe because the DNA of the target organism has been brought into close proximity with the lawn of oligonucleotides. Further, although the selection of a targets on the opposite sides of a double helical DNA molecule will theoretically have no effect on the sensitivity of the sensor, such a selection will not serve to optimally mitigate the steric hindrance effects. Steric hindrance effects still remain because if nucleic acid sequences are selected from opposite sides of a double helical molecule, the two molecules of target DNA in the hybridization mixture will be required to form two hybridized pairs. At any rate, the oligonucleotide sequences which are selected and synthesized should not consist of sections complementary to one another in view of the potential for the complementary probe molecules to bond with one another during assembly or after bonded to the electrode which would result in an incorrect signal from the detection device.

Although the accuracy of the probe is directly related to the length of the targeted oligonucleotide sequence, it is preferable to have oligonucleotides having shorter lengths on a probe which allows for rapid hybridization and diminishes the potential for mismatches, and steric hindrance. Although it is possible that an incorrectly matched base pair may exist in a hybridized stand, the presence of a mismatch will interfere with the electron transfer and effectively function as a resistor.

Oligonucleotides which complement the selected sequences are then synthesized in separate procedures according to techniques known by those skilled in the art. A plurality of such complementary oligonucleotides is synthesized for each target sequence. Next, using the techniques disclosed by Meade et al. in U.S. Pat. No. 5,874,046 the oligonucleotides complementary to the target sequences are next modified. See also International patent application 95/15971 entitled "Nucleic acid Mediated Electron Transfer) filed by Thomas Meade and Jon F. Kayyem and a paper by Messrs. Meade and Kayyem entitled "Electron Transfer Through DNA: Site modification of Duplex DNA with Ruthenium Donors and Acceptors," *Angew Chem. Int. Ed. Engl.*, Vol. 34, No. 3, pp. 352–354 (1995) (hereinafter the foregoing Mead et al. disclosures, which are hereby incorporated by reference). Nucleic acids may be modified by bonding a redox active moieties, such as a transition metal complex, which results in a molecule that is highly conductive. Transition metal complexes may be attached to the synthesized oligonucleotides using established biochemical techniques. See, e.g., Imazawa et al., J. Org. Chem., 44:2039 (1979); Hobbs et al, J. Org. Chem. 42(4): 714 (1977); Verheyden et al, J. Org. Chem., 36(2):250 (1971). These publications are hereby incorporated by reference. The donor and acceptor molecules are attached at predetermined locations near or at the ends of the synthesized strands.

Figure 4:
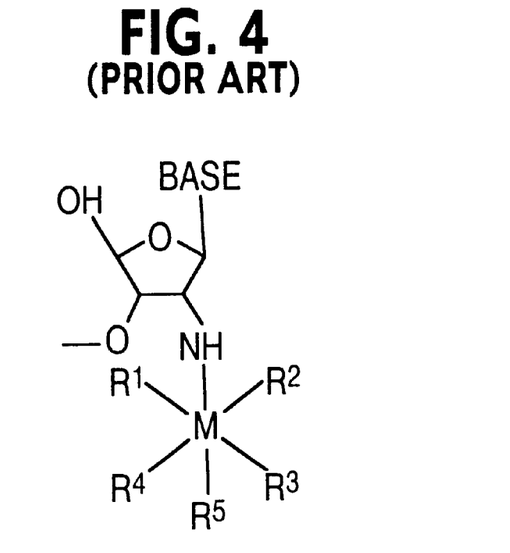
FIG. 4 is the general formula of a representative class of electron donor and acceptors which may be used in connection with the invention.
Figure 5:
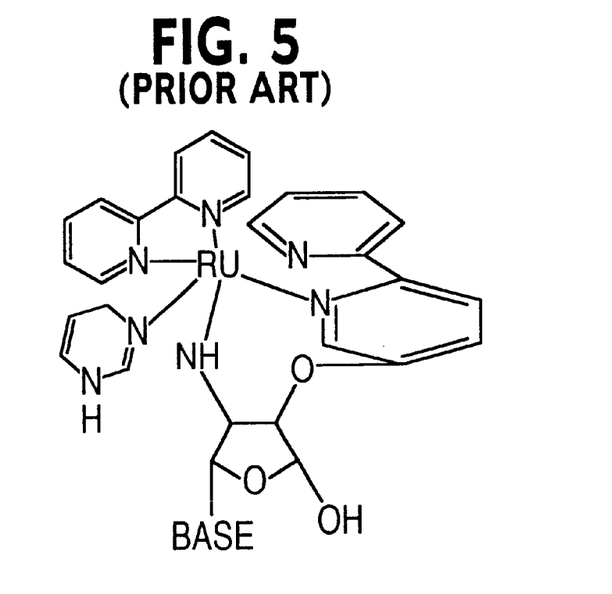
FIG. 5 is an example of a preferred ruthenium electron transfer donor using bisbipyridine and imidazole as the ligands.

FIG. 4 depicts the class of appropriate acceptor and donor moieties for attachment on the oligonucleotide. Although the number of possible donor moieties and acceptor moieties is very large, the preferred group is either ferrocene or ruthernium and FIG. 5 depicts a preferred embodiment wherein the ligands of a ruthenium electron transfer donor are bisbipyridine and imidazole.

Upon completion of the syntheses steps and modification with the redox moieties, the oligonucleotides are attached to electrode 30 within the sensor cell 14. One techniques employed is to release all the modified single-stranded oligonucleotides into solution to allow them to evenly distribute. A current is then applied to the electrode which attracts the oligonucleotide and a bond is formed. In a contemplated further embodiment, single stranded DNA probes may be coupled to carbolic acid groups of a polymer membrane by exocylic amines of the nucleobases which is in turn can be mechanically attached to an electrode using an O ring. See M. E. Napier, C. R. Loomis, M. F. Sistare, J. Kim, A. E. Eckhardt, H. H. Thorp (1997), "Probing 'Biomolecule Recognition with Electron Transfer: Electrochemical Sensors for DNA Hybridizatioin", *Bioconjugate Chem.*, Vol. 8, 906–913; Marchand-Brynaert, J. Deldime, M. Dupont, I. Dewez J.l., Schneider, Y/J. (1995), "Surface Functionalization of Poly(ethylene terephthalate) Film and Membrane by Controlled Wet Chemistry: Chemical Characterization of Carboxylated Surfaces", *J. Collolid Interface Sci.* 173, 236–244. (These publications are hereby incorporated by reference.). The resulting sensor cell incorporates a plurality of distinct groups of oligonucleotides evenly distributed across the surface of a working electrode.

In order to diminish the attraction and bonding of the neighboring oligonucleotides attached to the surface of the probe and to maintain the oligonucleotides in a substantially vertical orientation, an insulating layer may be provided adjacently to the base of the oligonucleotide molecules along the surface of the electrode. Examples of materials suitable for such applications include alkyl thiole or hexadiene. Such an insulating layer further serves to protect the surface of the electrode and diminish the flow of current through the hybridization mixture. The cell sensor component of the assembly is then integrated with the other components of the sensor assembly.

A feature of the modified oligonucleotides disclosed by Meade et al. is their enhanced conductivity when the oligonucleotide hybridizes with a complementary base pair and forms the characteristic double helical structure. In the helical form the molecule takes an orderly lattice like structure which results in the arrangement of the moieties at discrete distances from one another. The double helix molecule creates a highly conductive path which is postulated to proceed along its molecular axis between the electron donor and electron acceptor groups. Upon hybridization, the molecule forms the rigid double helix framework and it is believed that electrons travel through the $\pi$ orbitals of the stacked base pairs. It has been suggested that the incorporation of the moieties creates electron tunnels which have a high degree of conductivity.

An alternative mechanism is electron tunneling from DNA bound to the electrode by a complementary oligonucleotide to the "molecular wire" binding species, and thence to the electrode. The precise details of the electron transfer mechanism are not essential to this invention.

Electron transfer does not occur between electron donor and electron acceptor moieties in non-hybridized strands and, even if one of the base pairs is mismatched in the helical molecule the electrical conductivity will be very low as compared with a correctly paired base pair sequence. The actual rate of transfer is dependant on the distance between the electron acceptor and receptor pair, wherein longer the distance between the donor and acceptor, the slower the rate of transfer. The rate differentials are believed to be several orders of magnitude after the molecule has hybridized. Thus, the presence of double stranded nucleic acids can be determined by comparing the differences in electron transfer rates between hybridized and unhybridized molecules.

After sufficient time has elapsed to allow for hybridization, the detection sequence proceeds. According to a preferred embodiment of the invention electron transfer rates of the oligonucleotides are measured using cyclic voltammetry. Voltammetry broadly describes electrochemical technique that involves controlling the potential of an electrode while simultaneously measuring the current flowing at that electrode. In cyclic voltammetry, the working electrode potential is swept back and forth across the formal potential of the analyte. Repeated reduction and oxidation of the analyte causes alternating cathodic and anodic currents flow at the electrode. For an example of this technique see T. W. Welch, H. H. Thorp, J. Phys. Chem, 1996 100, 13829–13836, which is hereby incorporated by reference). Output from the potentiostat/galvanastat is directed to the microprocessor through and I/O port and analyzed by the microprocessor. The data is compared against a background scan of the buffer selected for the hybridization mixture, a scan which has been stored in the memory of the central processing unit. This background data may consist of previous measurements after the sensor has been deployed in a particular environment. The microprocessor thus receives data, reflecting current versus potential from the potentiostat, and analyses the data based upon historical data contained within the memory. The microprocessor generates an output signal indicating the presence or absence of the hybridized pairs. Since the data can reflect number of hybridized pairs, the output can also provide quantitative information regarding the existence of hybridized pairs.

The output signal from the microprocessor may be in the form of a visual display such as a LED, an audio alarm, or a flashing strobe light. It is contemplated that the device could be constructed to be worn by an individual and accordingly the device can incorporate a vibration, similar to a paging device, to alert the individual of the presence of a particular harmful bilogical agent. In a further contemplated embodiment an electromagnetic signal containing information relating to the status of the device is generated and transmitted to a receiver at a remote location.

Now referring back to FIG. 1, also included in the automated sensor assembly is a power source 68 which is used to power the detection device, the microprocessor, and process parameters such as the microfluidic controls which transfer the fluid within the assembly. The power source also is used in connection with the detection and regulation of temperatures within the sample preparation chamber and sensor cell. For example, when the device is stationed in extreme environments the temperature within the device must be maintained to allow for the flow of fluid through the device and to optimal hybridization temperatures.

After a predetermined time has elapsed and the detection sequence has been completed the process is reinitiated with the sample retrieval step thereby providing a continuous monitoring device. In an alternative embodiment, as soon as the hybridization mixture is introduced to the sensor cell, another sample is harvested and prepared so that when the hybridization step is complete for a first sample, a second sample may be immediately introduced into the sensor cell which displaces the first sample. An outlet port 70 returns the sample back to the environment.

Figure 6:
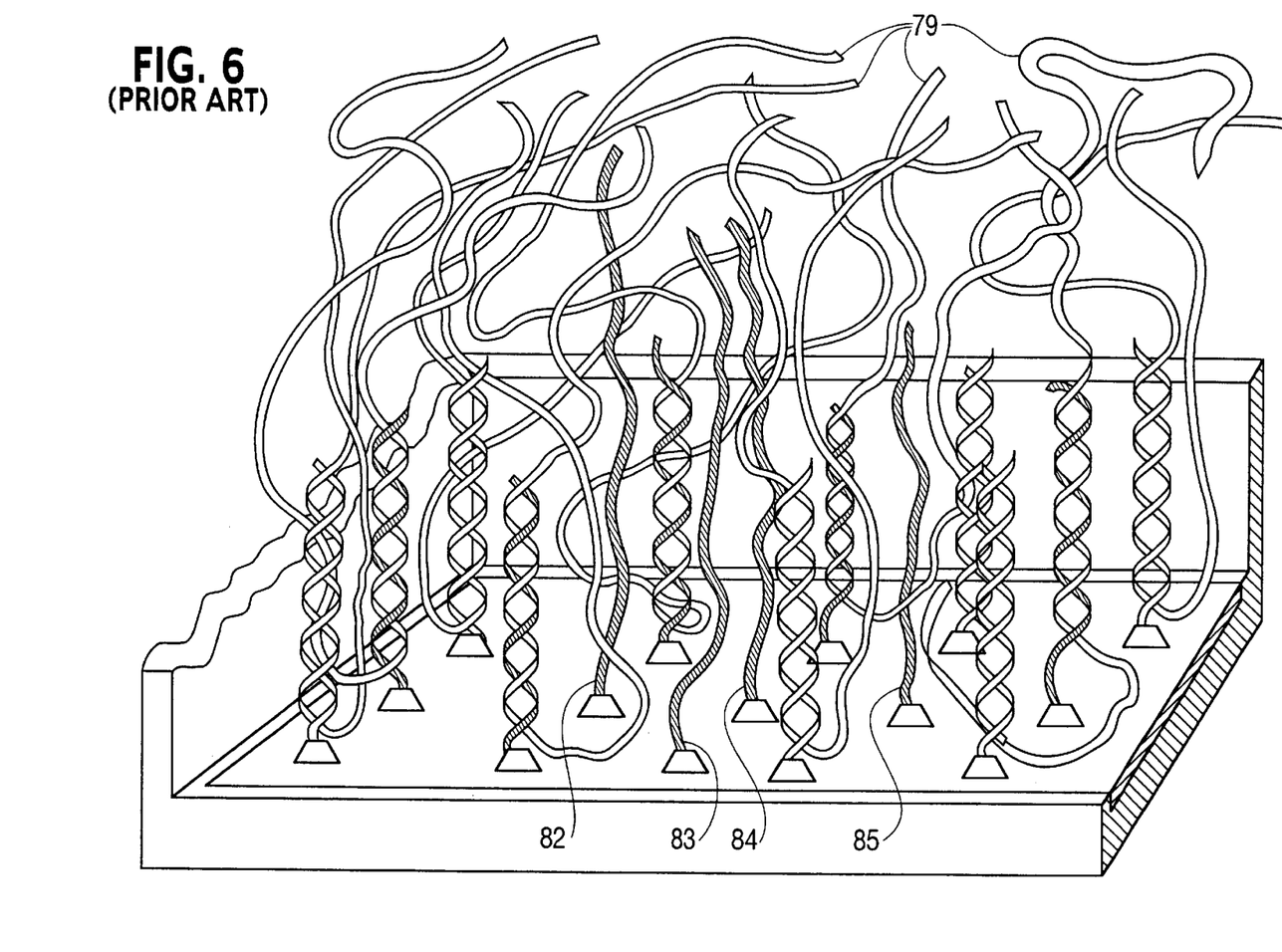
FIG. 6 is an illustration of a prior art sensor cell where the hybridization mixture has an abundance of target DNA.
Figure 7:
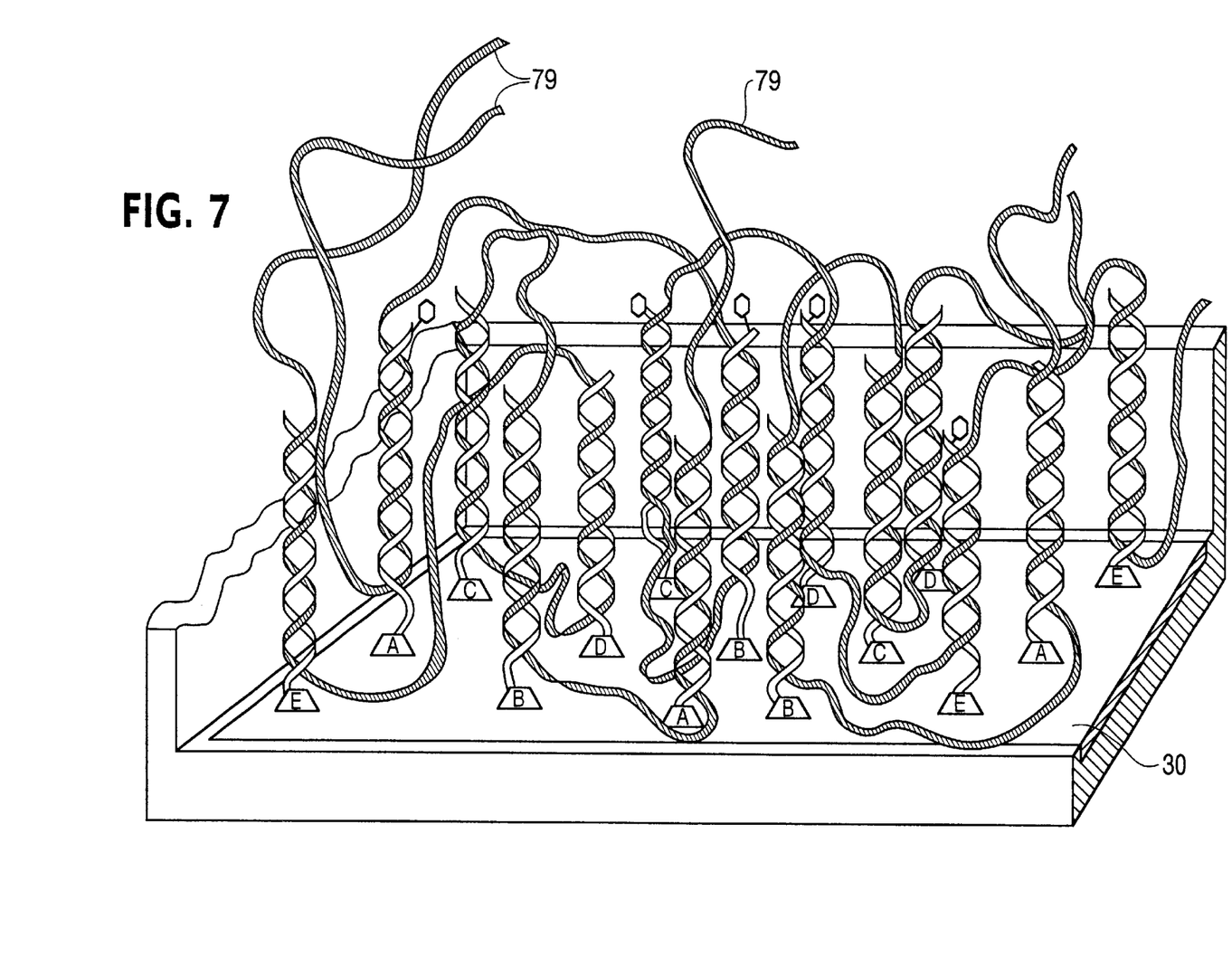
FIG. 7 is an illustration of a sensor cell according to the invention where the hybridization mixture has an abundance of target DNA.

When target DNA in a sample is available in large numbers, the invention does not necessarily accrue any particular advantage. In this regard, when DNA is abundant within the hybridization mixture the total number of molecules which will hybridize on the probe surface may be close to or the same as that which would hybridize on the prior art sensor cell depicted in FIG. 3. The voltammogram measured by the detector is principally affected by the total number of hybridized molecules on the electrode and, when target DNA is abundant, the measurements will be similar for both the cell according to the invention and the prior art cell. It is possible that the sensor cell of the present invention will offer a benefit even at high concentrations. DNA is a large molecule and, at high concentrations it may not be possible to physically fit enough target DNA molecules together over a single electrode to bind with all the oligonucleotide attached to the surface. Again, the non-hybridized sections of the target DNA molecules which extend on the opposite sides of the complementary sections, may physically obstruct other DNA molecules from binding on neighboring oligonucleotides. FIG. 6, illustrating the circumstances where a large number of target identical DNA molecules 79 are abundant interacting with a prior art probe, shows a number of oligonucleotides 82, 83 and 84 and 85 which have not hybridized due to steric hindrance. In FIG. 7, illustrating the circumstances where there is an abundance of target DNA 79 interacting with the sensor cell made according to the invention, the total number of hybridized pairs is greater due diminished steric hindrance. In the illustration all of the pairs are shown as hybridized. Regardless of the potential benefit in circumstances where there is an abundance of DNA, there is no disadvantage to the sensor cell according to the invention because the total number of hybridization pairs will not in any manner be diminished.

Since the detector hardware and electronics are identical regardless of the target organism, sensor cells having oligonucleotides complementary for a wide variety of target DNA sequences may be interchangeably used with the detection and electronic components of the assembly. In a preferred embodiment the sensor cells are interchangeable cartridges which contain all of the requisite process components for a particular target and contain other data for input to the microprocessor which identifies the target organism for the particular sensor cell and conveys information relating to the process parameters required by the target DNA.

When the sensor cell according to the invention is directed to medical assay applications or, in connection with genomic research, the sensor cell element and associated electronics may be employed independent of the automated sample capturing and preparation means. In medical assay techniques a sample may be prepared in the lab and then introduced to the cell sensor using conventional manual technologies such as pipetting.

The invention as described herein incorporates a single electrode containing a plurality of different groups modified oligonucleotides for a single target organism. A single assembly may further incorporate a plurality of independent sensor cells as described, each cell having a plurality of modified oligonucleotides and be directed to different target organisms. Such an assembly would be capable of generating an output based upon of a number of different anticipated target organisms. In such an arrangement, DNA targets having similar sample preparation and hybridization parameters could be combined allowing simultaneously and combined process steps for more than one target organism. The hybridization mixture would then be introduced to the hybridization chamber and, after a predetermined time has elapsed for hybridization, the detection step would proceed. The microprocessor 18 could then correlate the location of any sensor cell or sensor cells exhibiting enhanced electrical conductivity and generate the appropriate output to identify the presence of the existence of the target or target organisms in the sample.

In the event that the detection step does not detect a target DNA segment, the sample is release from the sensor cell after a predetermined interval and the operation as described would initiate once again. Although a number of specific embodiments have been described and illustrated herein, those having skill in the art will appreciate that there are additional arrangements and applications employing the invention which may be substituted for the specific disclosure as described herein. Having thus described the present invention and its preferred embodiment in detail, it will be readily apparent to those skilled in the art that further modifications to the invention may be made without departing from the spirit and scope of the invention as presently claimed.

I claim:

1. An improved sensor cell for the detection of the presence of DNA or RNA from a target organism comprising:

an electrode;

a plurality of different modified oligonucleotides attached to said electrode wherein said modification consists of the attachment of electron donor and electron acceptor moieties to the backbone of said oligoncleotides;

a plurality of target sequences of DNA or RNA in a target biological agent wherein each said target sequence is hybridized with two or more said modified oligonucleotides simultaneously in said sensor cell.

2. The sensor as recited in claim 1, wherein the number of said groups is between two and ten.

3. The sensor cell as recited in claim 1 wherein all of said target sequences comprise nucleotides characteristic of said target agent and are selected from the same strand of a single stranded DNA molecule.

4. The sensor cell as recited in claim 1 wherein said target agent is pathogentic to humans.

5. The sensor cell as recited in claim 1 wherein said target agent is prokaryotic organism or virus.

6. A biosensor assembly for the remote detection of the presence of nucleic acid sequences comprising:

a sensor cell comprising an electrode, a plurality of different modified oligonucleotides attached to said electrode and a plurality of target sequences of DNA or RNA in a target biological agent wherein said modification consists of the attachment of electron donor and electron acceptor moieties on the backbone of said oligoncleotides, said oligonucleotides complementary to a plurality of DNA or RNA target sequences from a target biological agent;

a sample preparation chamber for creating a hybridization solution, said chamber incorporating cell lysis means to rupture a cell membrane and release DNA into solution and denaturing means to reduce said DNA into single stranded catenate molecules;

flow control elements to introduce said hybridization mixture to said electrode;

electrochemical detection means, to determine if said hybridization mixture has bonded with said modified oligonucleotides and provide an output in response to the presences of a hybridized pair;

processor means to analyzes said output from said electrochemical detector means, and instruct said flow control elements;

communication means to convey information relating to the existence of hybridize molecules on the surface of said sensor cell;

and a power source, said power source for energizing said detection device, said processor means, said flow control elements and said communication means.

7. The biosensor assembly as recited in claim 6 further comprising sampling means to capture a sample from the environment and conveyance means to deliver said sample to said preparation chamber.

8. The biosensor assembly as recited in claim 7 wherein said sampling means further comprises a filter and means to backwash said filter.

9. The biosensor assembly as recited in claim 6 further comprising process operating condition detection elements and operating conditions control means, wherein said process operating condition detection elements sense conditions in said preparation chamber and said sensor cell and provide an input and, depending on responds by proving an input to said operating conditions control means.

10. The biosensor as recited in claim 9 wherein said operating condition elements comprises a temperature detection means and said operating conditions control means comprises temperature regulation means.

11. The biosensor assembly device as recited in claim 6 wherein said preparation chamber further comprises means to germinate endospores.

12. The biosensor assembly as recited in claim 6 further wherein said target biological agent is a prokaryotic organism.

13. The biosensor assembly as recited in claim 6 where said means to release target DNA further comprises employing osmotic pressure to lyse a cell membrane of said target biological agent.

14. The biosensor assembly as recited wherein said detection means further comprises a poteniostat.

15. The biosensor assembly as recited in claim 6 further wherein said microprocessor further provides an output relating to the presence or absence of a target DNA in said sample.

16. The biosensor assembly as recited in claim 15 wherein said output is an audible signal such as an alarm, an electric that can be remotely carried to a remote receiving device, an electromagnetic signal such as a radio signal, or an optical signal.

17. The biosensor assembly as recited in claim 6 where said moiety attached to said oligionucleotide groups is from a group consisting of ferrocene or ruthernium.

18. The biosensor assembly as recited in claim 6 wherein said sensor cell further comprises an insulating layer, a conducting layer, leads to said conducting layer.

* * * * *